(12) United States Patent
Tanaka et al.

(10) Patent No.: US 8,329,116 B2
(45) Date of Patent: Dec. 11, 2012

(54) MEASURING CHIP

(75) Inventors: Shuhei Tanaka, Kanagawa (JP);
Tomohiro Yamamoto, Osaka (JP);
Nobuhiko Ozaki, Kanagawa (JP);
Shinki Kojima, Kanagawa (JP)

(73) Assignee: Panasonic Corporation, Osaka (JP)

( * ) Notice: Subject to any disclaimer, the term of this patent is extended or adjusted under 35 U.S.C. 154(b) by 204 days.

(21) Appl. No.: 12/741,435

(22) PCT Filed: Nov. 21, 2008

(86) PCT No.: PCT/JP2008/003440
§ 371 (c)(1),
(2), (4) Date: May 5, 2010

(87) PCT Pub. No.: WO2009/066472
PCT Pub. Date: May 28, 2009

(65) Prior Publication Data
US 2010/0266452 A1    Oct. 21, 2010

(30) Foreign Application Priority Data
Nov. 21, 2007 (JP) .................................. 2007-301514

(51) Int. Cl.
*G01N 15/06* (2006.01)
*G01N 33/00* (2006.01)
*G01N 33/48* (2006.01)

(52) U.S. Cl. ...... 422/503; 422/50; 422/68.1; 422/82.01; 422/82.02; 436/43

(58) Field of Classification Search .................... 422/50, 422/68.1, 82.01, 82.02, 502, 503; 436/43
See application file for complete search history.

(56) References Cited

U.S. PATENT DOCUMENTS

| | | | |
|---|---|---|---|
| 2004/0115784 A1* | 6/2004 | Dzekunov | 435/173.6 |
| 2007/0077169 A1 | 4/2007 | Yang et al. | |
| 2010/0062414 A1 | 3/2010 | Yamamoto et al. | |

FOREIGN PATENT DOCUMENTS

| | | |
|---|---|---|
| JP | 05-288751 | 11/1993 |
| JP | 07-083928 | 3/1995 |
| JP | 2007-120983 | 5/2007 |
| JP | 2007-121275 | 5/2007 |

\* cited by examiner

*Primary Examiner* — Brian J Sines
(74) *Attorney, Agent, or Firm* — Greenblum & Bernstein, P.L.C.

(57) ABSTRACT

Provided is a measuring chip, which can spot a specimen liquid of a minute quantity for an immune agglutination easily and precisely to the measuring chip and which can prevent the flow of the specimen liquid and the contamination of the specimen. The measuring chip comprises at least two substrates, a spacer arranged between the substrates, at least one passage made of the substrates and the spacer into a hollow shape and having two open ends, counter electrodes for applying an electric field, and a specimen-spotted portion to be spotted with the specimen. The specimen-spotted portion has a structure made of a square, circular, elliptical or sector shape by that spacer. Moreover, the specimen-spotted portion has two open ends, one of which is connected to one open end of that passage.

8 Claims, 10 Drawing Sheets

MEASURING CHIP

TECHNICAL FIELD

The present invention relates to a measuring chip that measures and detects a biologically specifically reactive substance in a sample liquid using a biologically specific agglutination reaction, and the shape of a sample deposition part of the measuring chip. More particularly, the present invention relates to a technique of a measuring chip that makes it possible to deposit a very small amount of a sample liquid for an antigen-antibody agglutination reaction on the measuring chip easily and accurately, and to prevent the sample liquid from flowing and cross contamination of sample liquids.

BACKGROUND ART

To detect a test substance in a sample liquid, many conventional methods of using an antibody that can specifically bind with a test substance are devised. One of such methods is to optically detect immune aggregate generated by an antigen-antibody reaction.

With this method, first, a predetermined amount of an antibody that can specifically bind with a test substance is added to a sample liquid containing the test substance, to form aggregate. Next, upon radiating light to the sample liquid containing the aggregate, the light is scattered by hitting the aggregate, so that the amount of light passing through the sample liquid changes. The change of the amount of light is known by measuring either transmitted light, reflected light or scattered light.

Generally, although a turbidimetric immunoassay which involves measuring transmitted light and a nephelometric immunoassay which involves measuring scattered light are distinguished, these two measurement methods have the same detection principle of observing the influence of light scattering by aggregate. The amount of aggregate changes in proportion to the concentration of a test substance, so that, it is possible to find the concentration of a test substance by measuring either transmitted light, reflected light or scattered light.

A method of making these methods more sensitive is the latex agglutination assay. In the latex agglutination assay, antibodies are immobilized on latex particles. When a test substance is bound with the antibodies, aggregate of latex particles is formed. The aggregate of latex particles allows light to scatter much more than aggregate consisting of antigens and antibodies, so that highly sensitive detection is possible.

Figure 1:
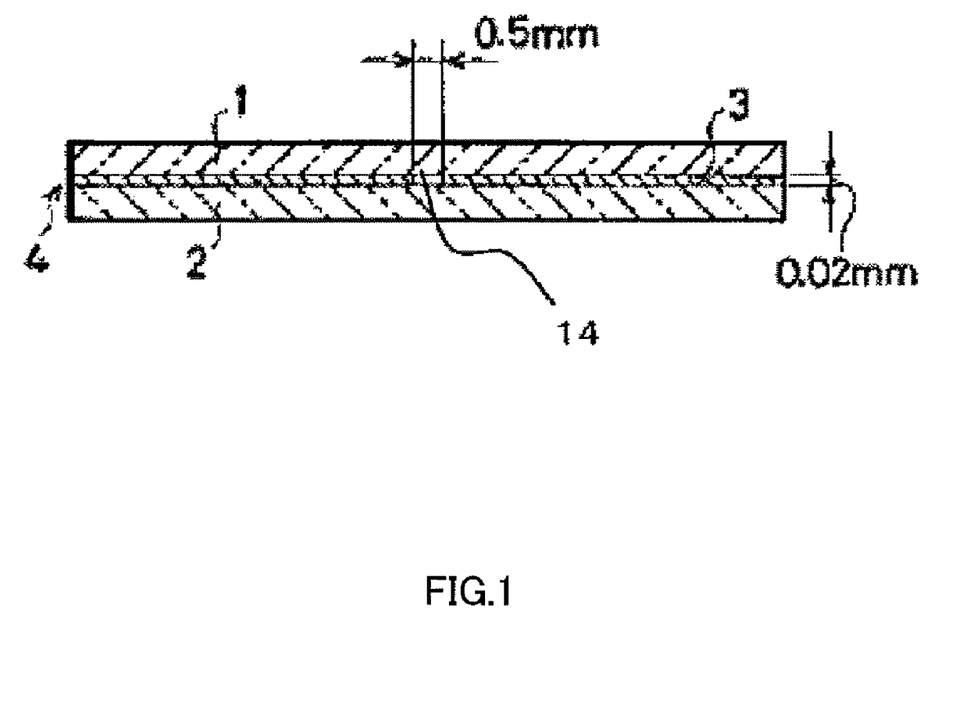
FIG. 1 is a cross-sectional view of a conventional biologically specific reaction chip.
Figure 2:
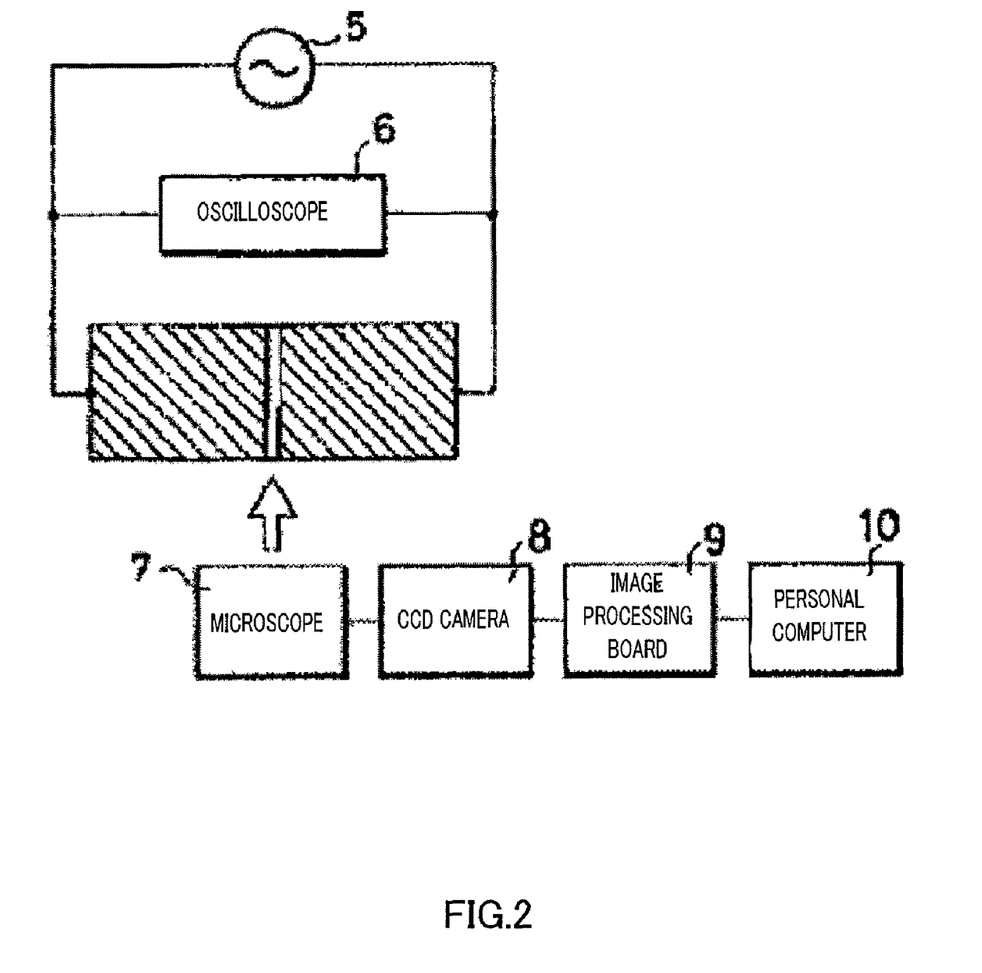
FIG. 2 is a block diagram of a conventional system in which a biologically specifically reactive substance is detected or measured.
Figure 3:
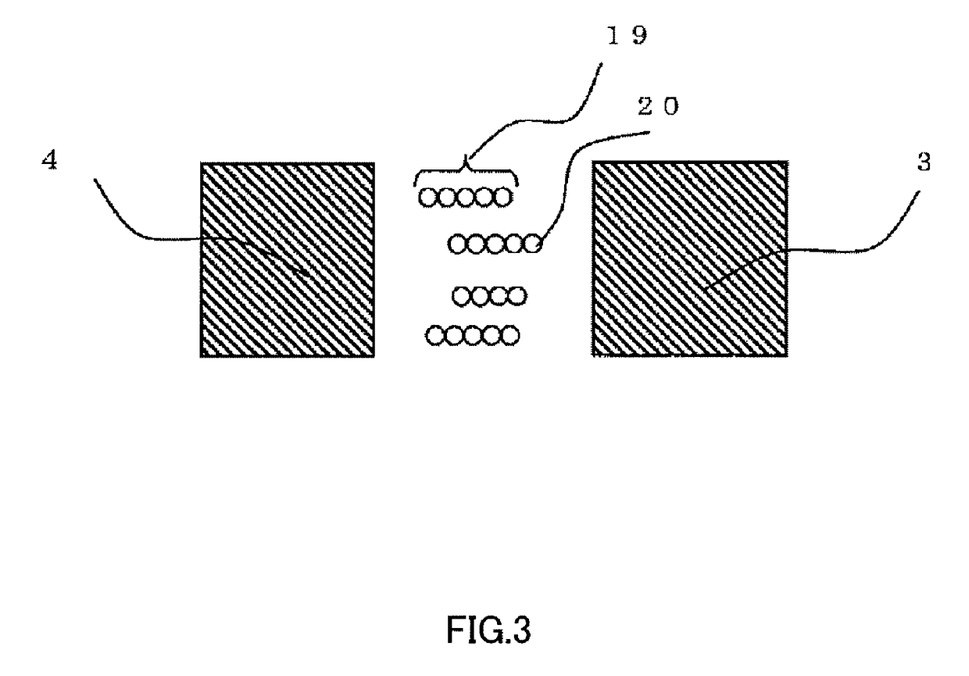
FIG. 3 is an exploded view of electrode parts of a conventional biologically specific reaction chip upon application of voltage.
Figure 4:
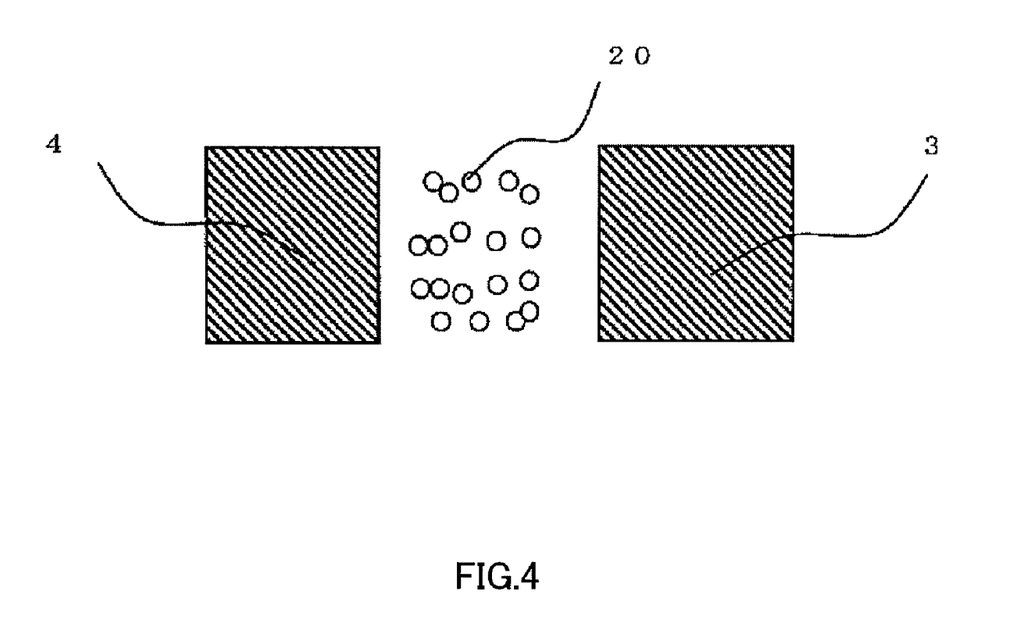
FIG. 4 is an exploded view of electrode parts of a conventional biologically specific reaction chip upon stop of application of voltage.

Patent Document 1 discloses the method of making the latex agglutination assay more sensitive. The measurement apparatus and the measurement method disclosed in Patent Document 1 will be explained with reference to FIGS. 1 to 4. FIG. 1 is a cross-sectional view of a reaction chip, FIG. 2 is a block diagram of a reaction measurement apparatus, and FIGS. 3 and 4 are exploded views of electrode parts of a reaction chip. Electrodes 3 and 4 having a thickness of 0.02 mm are interposed between slide glasses 1 and 2 so that the distance between electrodes 3 and 4 is 0.5 mm. Latex particles 20 are dispersed in a sample liquid in flow path 14 surrounded by slide glasses 1 and 2 and electrodes 3 and 4. By applying an alternating voltage to electrodes 3 and 4 using alternating power source supplying apparatus 5 and applying an electric field to the above reaction system, a phenomenon referred to as "pearl chaining" (19) where latex particles 20 are aligned linearly occurs.

After that, when application of the electric field is stopped, latex particles 20 that have been aligned linearly disperse again. If the test substance (antigen) is present upon pearl chaining, latex particles 20 do not disperse again even after application of the electric field is stopped, and pearl-chained particles still exist. Consequently, by measuring the state of aggregate of latex particles 20 not dispersing again even after application of an electric field is stopped, that is, by measuring the state of aggregate of latex particles aggregating by an antigen-antibody reaction using an image process apparatus configured with microscope 7, CCD camera 8, image processing board 9 and personal computer 10, it is possible to detect or measure a test substance (antigen).
Patent Document 1: Japanese Patent Application Laid-Open No. 07-83928

DISCLOSURE OF INVENTION

Problems to be Solved by the Invention

However, the above-described conventional measuring chip does not have an independent sample deposition structure in the chip. One edge of a slide-glass substrate is aligned with an aperture end of the flow path; no deposition part is formed. Therefore, a sample liquid should be deposited directly in the flow path. Consequently, there is a problem with the above-described conventional measuring chip, that it is difficult to deposit the sample. Further, by letting the deposited sample liquid flow down the walls of the deposition part, a certain amount of the sample liquid does not flow in the flow path, and, upon application of voltage, the sample liquid reacts on the ends of electrodes to produce heat, and causes another problem of interfering with measurement. Furthermore, when there are a plurality of flow paths in one measuring chip, by letting a deposited sample liquid flow down the walls of the deposition part, cross contamination of sample liquids occurs between neighboring flow paths. Therefore, there is another problem that measurement cannot be conducted accurately.

It is therefore an object of the present invention to provide a measuring chip that is able to solve the above-described problems, and that measures and detects a biologically specifically reactive substance in a sample liquid using a biologically specific agglutination reaction. By this means, it is possible to measure a test substance in a very small amount of a sample liquid fast, easily and accurately using an antigen-antibody agglutination reaction in particular.

Means for Solving the Problem

The present invention provides a measuring chip for biologically specifically reactive substance in which an alternating current is applied to electrodes and adopts a configuration including: a sample deposition part in which a sample is deposited; at least two substrates; a spacer disposed between the substrates; at least one flow path that is formed with the substrates and the spacer, and that has a hollow shape and aperture ends at both ends; and a pair of electrodes for which an electric field is applied, wherein the sample deposition part has a shape of a quadrilateral, circle, oval or sector.

By this configuration, it is possible to deposit a very small amount of a sample liquid for an antigen-antibody agglutination reaction on the measuring chip easily and accurately, and to prevent the sample liquid from flowing and cross contamination of sample liquids.

Advantageous Effects of Invention

According to the present invention, it is possible to deposit a very small amount of a sample liquid on the measuring chip easily and accurately, and to prevent the sample liquid from flowing and cross contamination of sample liquids.

BEST MODE FOR CARRYING OUT THE INVENTION

Now, embodiments of the present invention will be described in detail with reference to the accompanying drawings.

Embodiment 1

Figure 5:
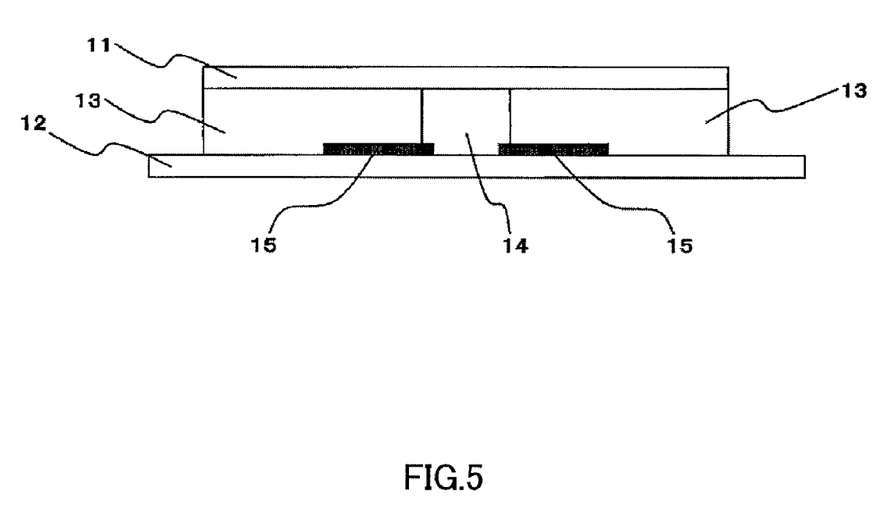
FIG. 5 is a cross-sectional view of one aspect of the measuring chip for a biologically specifically reactive substance according to Embodiment 1.
Figure 6:
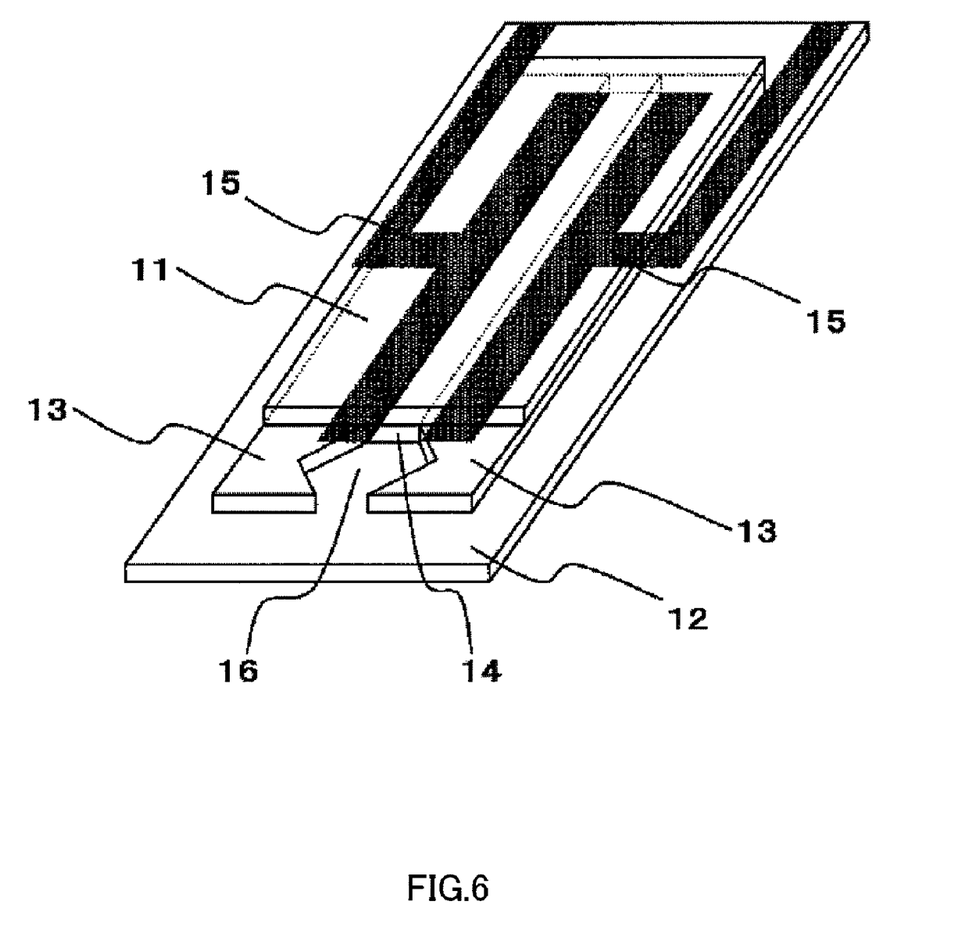
FIG. 6 is a perspective view of one aspect of the measuring chip for a biologically specifically reactive substance according to Embodiment 1.

First, the measuring chip of the present invention will be explained with reference to FIGS. 5 and 6. FIG. 5 is a cross-sectional view of the measuring chip showing an embodiment of the present invention. FIG. 6 is a perspective view of the measuring chip showing an embodiment of the present invention.

The measuring chip of the present invention has glass substrate 12 on which a pair of electrodes 15 distant from each other 500 μm or less are formed and glass substrate 11. Glass substrates 11 and 12 are disposed to oppose each other across spacer 13 having a thickness of 7 to 10 μm, to form flow path 14 in which a sample liquid flows. Both ends of flow path 14 are aperture ends.

The material of electrodes 15 is not particularly limited as long as the material is conductive, and is inorganic substances including gold, silver and copper, for example. The method of forming electrodes 15 on glass substrate 12 is not particularly limited, and is selected from a sputtering method, printing method and dip coating method, for example.

A pair of electrodes 15 have parallel patterns, and, as shown in FIG. 6, have terminals to be connected with an external apparatus. The shape of the terminals is not particularly limited as long as the terminals are connectable with an external apparatus, and is not limited to the shape shown in FIG. 6.

Spacer 13 forms flow path 14 and is a member to prevent a sample liquid from leaking when the sample liquid is injected. Further, as shown in FIG. 6, spacer 13 is a member to form sample deposition part 16. The material and the forming method of spacer 13 are not limited. For example, spacer 13 is formed by attaching glass substrates 11 and 12 such that an adhesive double-sided sheet from which a given shape is extracted are interposed.

Sample deposition part 16 has a quadrilateral shape as shown in FIG. 6, has at least two open ends. One open end of sample deposition part 16 is connected with one aperture end of flow path 14. The shape of the opening in sample deposition part 16 is not limited to the quadrilateral shape shown in FIG. 6. The shape of the opening in sample deposition part 16 is preferably a quadrilateral shape, circle shape, oval shape or sector shape, because sample deposition part 16 having shape of a quadrilateral, circle, oval or sector are relatively easier to manufacture than more complicated shapes, and a sample liquid become less likely to remain on the walls of sample deposition part 16 and flows in flow path 14 smoothly.

A conventional measuring chip does not have an independent sample deposition structure in the chip as shown in FIGS. 1 and 2. One edge of a slide-glass substrate is aligned with an aperture end of the flow path; no deposition part is formed. Therefore a sample liquid should be deposited directly in the flow path. Consequently, there is a problem with a conventional measuring chip, that it is difficult to deposit the sample.

Further, by letting the deposited sample liquid flow down the walls of the deposition part, a certain amount of the sample liquid does not flow in the flow path, and, upon application of voltage, the sample liquid reacts on the ends of electrodes to produce heat, and causes another problem of interfering with measurement. Furthermore, when there are a plurality of flow paths in one measuring chip, by letting a deposited sample liquid flow down the walls of the deposition part, cross contamination of sample liquids occurs between neighboring flow paths. Therefore there is another problem that measurement cannot be conducted accurately.

Figure 7:
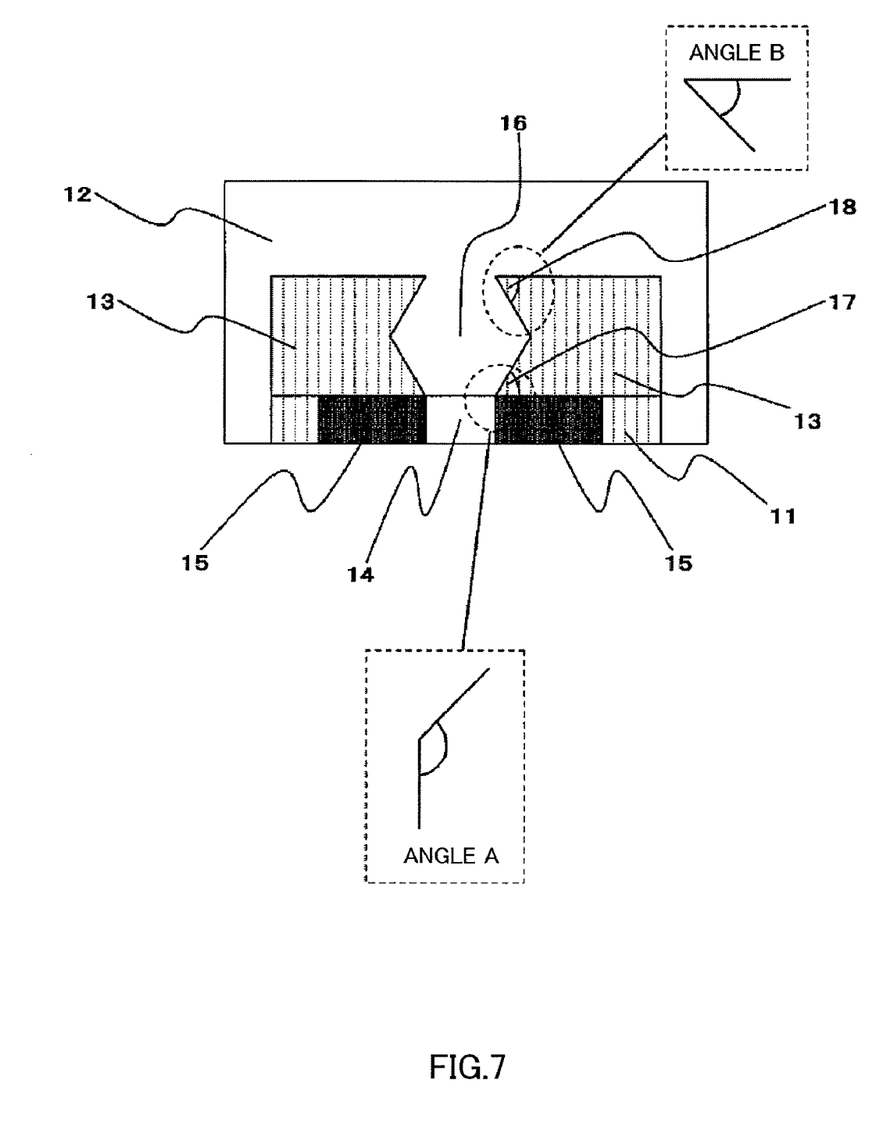
FIG. 7 is a plan view of one aspect of the measuring chip for a biologically specifically reactive substance according to Embodiment 1.

FIG. 7 shows a plan view of one aspect of the measuring chip of the present invention to solve the above these problems. Enlarged views of broken line circles in the figure are shown within frames indicated by broken line quadrilaterals. Angles A and B are shown within the frames.

As shown in FIG. 7, sample deposition part 16 is formed by cutting out a quadrilateral shape from spacers such that two angles A 17 each formed between one open end of sample deposition part 16 and the connected flow path 14 are more than 90° and equal to or less than 180° (90° is not included, that is, a case where the width of open ends of sample deposition part 16 connected with flow path 14 is more than the width of flow path 14, is excluded) and two angles B 18 formed at the other opening end of sample deposition part 16 are less than 90°. By making angles A 17 and angles B 18 within the above ranges, it is possible to define the shape of sample deposition part 16 in a quadrilateral shape, circle shape, oval shape or sector shape and prevent a sample liquid from flowing down the walls of upper glass substrate 11 and spacers 13.

The shape of sample deposition part 16 may be, for example, a square, rectangle, rhombus, trapezoid or parallelogram, and may be any quadrilateral defined by the above-described angles A 17 and angles B 18. Further, the open end not connected with flow path 14 in sample deposition part 16 is preferably not closed and of the width of the open end is preferably smaller than the length of the diagonal line between the two vertices that do not form the open ends in the deposition part. Further, it is preferable that the width of the flow path and the width of the sample deposition part are not the same. That is, the width of the open end not connected with flow path 14 in sample deposition part 16 is preferably longer than 0 μm and less than the length of the diagonal line between two vertices not forming the open ends. If the open end not connected with flow path 14 in sample deposition part 16 is closed, it is possible that a sample liquid has difficulty in flowing in flow path 14 from the liquid pool when the sample liquid is deposited in deposition part 16. However, by providing an open end, it is possible to introduce a sample liquid to flow path 14 fast.

As a result of depositing a sample liquid containing latex particles in the deposition part of the chip according to the present embodiment, it has been confirmed that the sample liquid is injected into the flow path without flowing down the walls of spacers.

Embodiment 2

Figure 8:
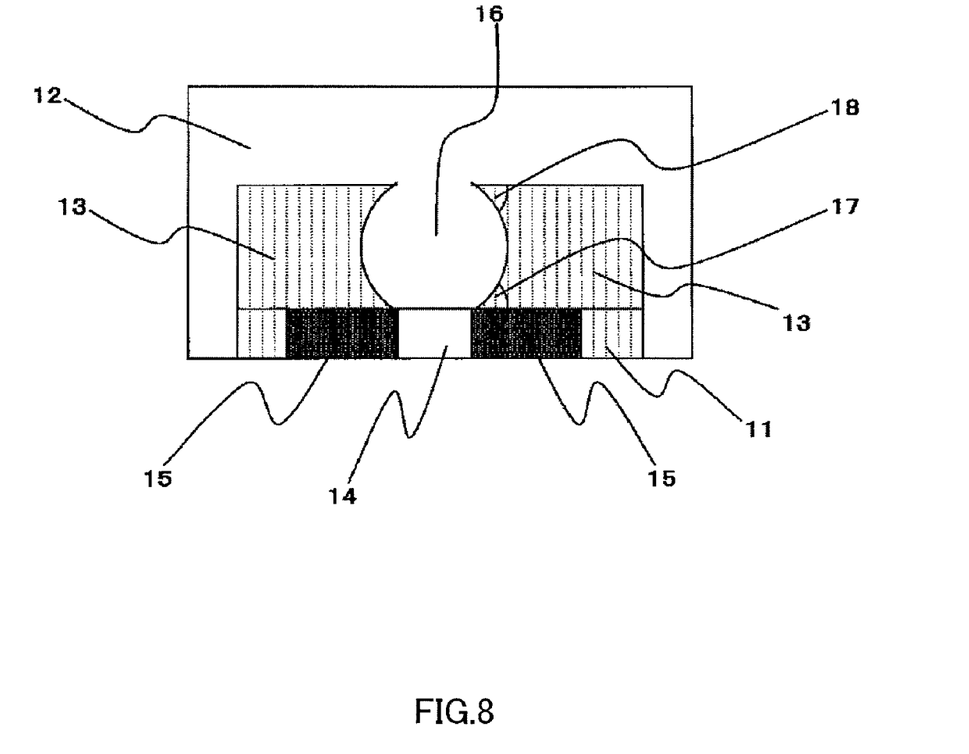
FIG. 8 is a plan view of one aspect of the measuring chip for a biologically specifically reactive substance according to Embodiment 2.

FIG. 8 shows a plan view of the measuring chip representing the present embodiment. Although FIG. 8 is substantially the same as FIG. 6 in the configuration of the chip shown in Embodiment 1, FIG. 8 differs from FIG. 6 in the shape of sample deposition part 16.

As shown in FIG. 8, sample deposition part 16 is formed by cutting out a circle shape from spacers such that two angles A 17 each formed between one open end of sample deposition part 16 and the connected flow path 14 are more than 90° and equal to or less than 180° (90°<A≦180°) and two angles B 18 formed at the other open end of sample deposition part 16 are less than 90° (0°<B<90°).

The shape of sample deposition part 16 may be any circle shape defined by the above-described angles A 17 and angles B 18. Further, the two open ends are placed in two points at which the circle and a straight line are crossed. Furthermore, it is preferable that the width of the open end not connected with flow path 14 in sample deposition part 16 is more than 0 μm and less than the diameter of the circle in sample deposition part 16.

As a result of depositing a sample liquid containing latex particles in the deposition part of the chip according to the present embodiment, it has been confirmed that the sample liquid is injected into the flow path without flowing down the walls of spacers.

Embodiment 3

Figure 9:
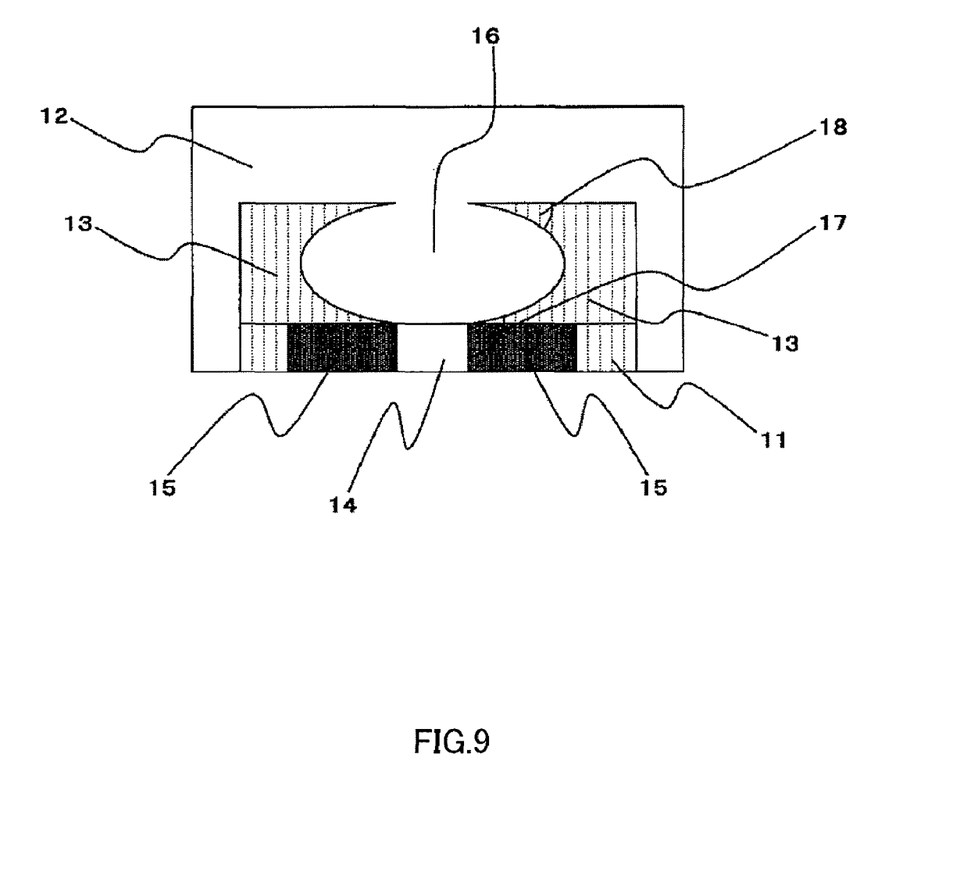
FIG. 9 is a plan view of one aspect of the measuring chip for a biologically specifically reactive substance according to Embodiment 3.

FIG. 9 shows a plan view of the measuring chip representing the present embodiment. Although FIG. 9 is substantially the same as FIG. 6 in the configuration of the chip shown in Embodiment 1, FIG. 9 differs from FIG. 6 in the shape of sample deposition part 16.

As shown in FIG. 9, sample deposition part 16 is formed by cutting out an oval shape from spacers such that two angles A 17 each formed between one open end of sample deposition part 16 and the connected flow path 14 are more than 90° and equal to or less than 180° (90°<A≦180°) and two angles B 18 formed at the other opening end of sample deposition part 16 are less than 90° (0°<B<90°).

The shape of sample deposition part 16 may be any oval shape defined by the above-described angles A 17 and angles B 18. Further, the two open ends are placed in two points at which the oval and the major axis or minor axis of the oval cross. Furthermore, it is preferable that the width of the open end not connected with flow path 14 in sample deposition part 16 is more than 0 μm and less than the length of the major axis or the length of the minor axis of the oval in sample deposition part 16.

As a result of depositing a sample liquid containing latex particles in the deposition part of the chip according to the present embodiment, it has been confirmed that the sample liquid is injected into the flow path without flowing out from the walls of spacers.

Embodiment 4

Figure 10:
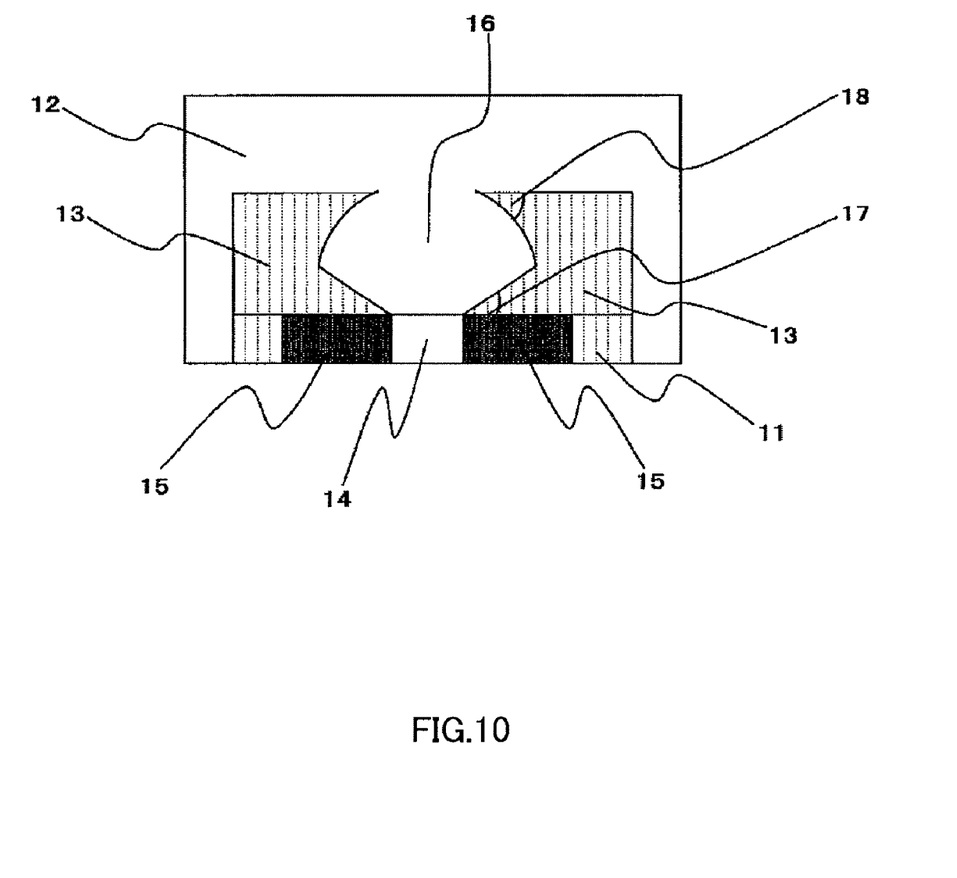
FIG. 10 is a plan view of one aspect of the measuring chip for a biologically specifically reactive substance according to Embodiment 4.

FIG. 10 shows a plan view of the measuring chip representing the present embodiment. Although FIG. 10 is substantially the same as FIG. 6 in the configuration of the chip shown in Embodiment 1, FIG. 10 differs from FIG. 6 in the shape of sample deposition part 16.

As shown in FIG. 10, sample deposition part 16 is formed by cutting out a sector shape from spacers such that two angles A 17 each formed between one open end of sample deposition part 16 and the connected flow path 14 are more than 90° and equal to or less than 180° (90°<A≦180°) and two angles B 18 formed at the other opening end of sample deposition part 16 are less than 90° (0°<B<90°).

The shape of sample deposition part 16 may be any sector shape defined by the above-described angles A 17 and angles B 18. Further, the open ends are placed in the following points A and B.

Point A: a vertex formed with two sides of the sector shape.
Point B: a point at which an arc of the sector shape crosses a straight line, which passes an arc of the sector and the vertex formed with the two sides of the sector. It is preferable that the width of the open end not connected with flow path 14 in sample deposition part 16 is more than 0 μm and less than the interval between the two vertices formed with the arc of the sector shape and the sides of the sector shape.

In the above-described embodiments, the spacers may be subject to hydrophobic treatment. Further one device structure having substrates, spacer, flow path and a pair of electrodes may be disposed in one chip. Further, at least two measuring chips having substrates, spacer, flow path, sample deposition part and a pair of electrodes may be disposed in one measuring chip.

The disclosure of Japanese Patent Application No. 2007-301514, filed on Nov. 21, 2007, including the specification, drawings and abstract, is incorporated herein by reference in its entirety.

INDUSTRIAL APPLICABILITY

The measuring chip according to the present invention makes it possible to deposit a very small amount of a sample liquid for an antigen-antibody agglutination reaction on the measuring chip easily and accurately, and to prevent the sample liquid from flowing and cross contamination of sample liquids. The measuring chip according to the present invention is suitable for use in measuring chips that conduct measurement and detection using a biologically specific agglutination reaction, and, in particular, measuring chips that measure a very small amount of a sample liquid for an antigen-antibody agglutination reaction easily and accurately.

EXPLANATION OF REFERENCE NUMERALS 1, 2 SLIDE GLASS
3, 4 ELECTRODE

5 ALTERNATING POWER SOURCE SUPPLYING APPARATUS
6 OSCILLOSCOPE
7 FLUORESCENCE MICROSCOPE
8 CCD CAMERA
9 IMAGE PROCESSING BOARD
10 PERSONAL COMPUTER
11 UPPER COVER GLASS SUBSTRATE
12 GLASS SUBSTRATE
13 SPACER
14 FLOW PATH
15 ELECTRODE
16 SAMPLE DEPOSITION PART
17 ANGLE A
18 ANGLE B
19 PEARL CHAIN
20 LATEX PARTICLES

The invention claimed is:

1. A measuring chip for a biologically specifically reactive substance in which an alternating current is applied to electrodes, the measuring chip comprising:
   two substrates;
   a spacer coupled to and disposed between the substrates;
   at least one flow path extending through the spacer, the substrates and the spacer comprising the flow path, the flow path having a hollow configuration and having a first aperture end and a second aperture end;
   a sample deposition part in which a sample is deposited, the sample deposition part provided in the spacer and coupled to the at least one flow path, the sample deposition part having a first open end and a second open end and being independent from the first aperture end and the second aperture end, the first open end being connected with the first aperture end; and
   a pair of electrodes to which an electric field is applied, the pair of electrodes arranged within the at least one flow path, wherein:
   an angle A is provided in the spacer between the first open end and the first aperture end, the angle A is more than 90° and no more than 180°, and
   an angle B is provided in the spacer at the second open end, the angle B is more than 0° and less than 90°.

2. The measuring chip according to claim 1, wherein the sample deposition part is constituted with the spacer and one of the two substrates.

3. The measuring chip according to claim 1, wherein the sample deposition part has a shape of a quadrilateral, circle, oval or sector.

4. The measuring chip according to claim 1, wherein the second open end is not closed.

5. The measuring chip according to claim 1, wherein the width of the flow path and the width of the sample deposition part are different each other.

6. The measuring chip according to claim 1, wherein the spacer is subject to hydrophobic treatment.

7. A measuring chip structure comprising one measuring chip according to claim 1 disposed in one chip.

8. A measuring chip structure comprising at least two measuring chips according to claim 1 disposed in one chip.

* * * * *